United States Patent [19]

Mathiowitz et al.

[11] Patent Number: 4,898,734
[45] Date of Patent: Feb. 6, 1990

[54] POLYMER COMPOSITE FOR CONTROLLED RELEASE OR MEMBRANE FORMATION

[75] Inventors: Edith Mathiowitz, Brookline; Robert S. Langer, Somerville, both of Mass.; Abraham Warshawsky, Rehovot, Israel; Elazar Edelman, Brookline, Mass.

[73] Assignee: Massachusetts Institute of Technology, Cambridge, Mass.

[21] Appl. No.: 162,161

[22] Filed: Feb. 29, 1988

[51] Int. Cl.$^4$ ................................................. A61F 2/00
[52] U.S. Cl. ..................................... 424/426; 424/422; 424/469; 424/486; 424/487
[58] Field of Search ............... 424/426, 422, 486, 484, 424/469, 487

[56] References Cited

U.S. PATENT DOCUMENTS

| | | | |
|---|---|---|---|
| 2,996,431 | 8/1961 | Barry | 424/469 X |
| 3,464,413 | 9/1969 | Goldfarb et al. | 128/268 |
| 3,887,699 | 6/1975 | Yolles | 424/426 X |
| 3,904,444 | 9/1975 | Anderson et al. | 424/486 X |
| 3,921,636 | 11/1975 | Zaffaroni | 424/486 X |
| 3,992,518 | 11/1976 | Chien et al. | 424/486 X |
| 4,070,347 | 1/1978 | Schmitt | 424/426 X |
| 4,164,560 | 8/1979 | Folkman et al. | 424/486 |
| 4,272,398 | 6/1981 | Jaffe | 424/78 X |
| 4,277,364 | 7/1981 | Shasha et al. | 424/486 X |
| 4,351,337 | 9/1982 | Sidman | 424/426 X |
| 4,352,883 | 10/1982 | Lim | 435/178 |
| 4,642,233 | 2/1987 | Urquhart et al. | 424/486 X |
| 4,741,872 | 5/1988 | DeLuca et al. | 424/486 X |

OTHER PUBLICATIONS

Beck, et al., "A New Long Acting Injectable Microcapsule System for the Administration of Progesterone", *Fertility and Sterility*, 31 (5), 545 (1979).
Benita, et al., "Characterization of Drug Loaded Poly(d,1-Lactide) Microspheres", *J. Pharm. Sci.*, 73, 1721 (1984).
Kost, et al., "Ultrasonic Modulated Drug Delivery System", *Polymers in Medicine: Biomedical and Pharmaceutical Applications* 2, E. Schellini, Editor (1987).
Kwong, et al., "In Vitro and In Vivo Release of Insulin From Poly (Lactic Acid) Microbeads and Pellets", *Journal of Controlled Release*, 4, 47 (1986).

(List continued on next page.)

Primary Examiner—Thurman K. Page
Attorney, Agent, or Firm—Kilpatrick & Cody

[57] ABSTRACT

The present invention is a method to produce novel composites based on microcapsules or microspheres embedded in contiuous polymeric matrices. Both non-bioerodible and erodible polymers can be used. Material can be incorporated into the microcapsules or microspheres for subsequent release. In one embodiment of the present invention, spheres are homogeneously dispersed in a polymer matrix and then forced to release their contents by exposure to temperature, light or ultrasound. Alternatively, polymers which degrade as a function of time or hydrolysis can be used for controlled releases. The polymer composites have completely different properties from either a continuous polymer matrix or microcapsules or microspheres and are therefore useful for a wide variety of applications. When carbon tetrachloride is the incorporated material, the film is useful as a flame retarding device. When foaming agents are used, especially UV or heat sensitive materials, gas can be evolved inside each capsule to form bubbles in the polymer. When a drug or other bioactive agent is incorporated in the spheres and encapsulated with the polymer, release occurs only through the eroded or ruptured spheres. In contrast to release from encapsulated microcapsules, release from the polymer composite is approximately linear with time. Erosion of the polymer spheres can also be used to create a porous polymeric structure. This kind of device can be used in transdermal drug delivery, vascular grafts, wound-healing films, or as a polymeric porous membrane.

16 Claims, 5 Drawing Sheets

OTHER PUBLICATIONS

Leong, et al., "Bioerodable Polyanhydrides as Drug Carrier Matrices, 1, Characterization, Degradation, and Release Characteristics", *Journal of Biomedical Materials Research*, 19, 941 (1985).

Mathiowitz and Langer, "Polyanhydride Microspheres as Drug Carriers, 1, Hot Melt Microencapsulation", *Journal of Controlled Release*, 5, 13, (1987).

Mathiowitz, et al., "Macromolecular Drug Release From Biodegradable Polyanhydride Microspheres", Proceed. Intern. Symp. Control. Rel. Bioact. Mater., 12, 183 (1985).

Mathiowitz, et al., "Photochemical Rupture of Microcapsules: A Model System", Journal of Applied Polymer Science, 26, 809 (1981).

Mathiowitz, et al., "Polyanhydride Microspheres as Drug Carriers. 2. Microencapsulation by Solvent Removal", Journal of Applied Polymer Science, 35, 755 (1988).

Yolles, et al., "Controlled Release of Biologically Active Agents", *Controlled Release Polymeric formulation*, D. R. Paul and F. W. Harris, Editors, American Chemical Society Symposium, Washington, D.C. 33, 123 (1976).

Mathiowitz, Ph.D. Thesis, Weizmann Institute of Science, Rehovot, Israel, 1984.

Setterstrom, et al., "Controlled Release of Antibiotics from Biodegradable Microcapsules for Wound Infection Control", Proceedings of the 1982 Army Science Conference, U.S. Military Academy, West Point, N.Y., Jun. 1982.

POLYMER COMPOSITE FOR CONTROLLED RELEASE OR MEMBRANE FORMATION

The Government has rights in this invention pursuant to Grant Number 5-R01-GM26698 awarded by the Department of Health and Human Services.

BACKGROUND OF THE INVENTION

The present invention is generally in the area of polymeric matrices containing microspheres or microcapsules for controlled release of encapsulated compounds or modification of the polymer matrix.

The use of microcapsules for controlled drug delivery or implantation of cells or other materials into a patient is well known. For example, U.S. Pat. No. 4,352,883 to Lim describes the microencapsulation of a variety of substances. U.S. Pat. No. 3,464,413 to Goldfarb et al. discloses bandages containing microcapsules which release drugs when ruptured. Similarly, the use of biocompatible, bioerodible polymeric implants, such as the devices made from polyglycolic acid, polylactic acid or polyanhydrides, are also well known. K. W. Leong et al describe the use of polyanhydride implants for controlled drug delivery in "Bioerodible polyanhydrides as drug-carrier matrices. I: Characterization, degradation, and release characteristics", *J. Biomedical Mater.*, 19,941–955 (1985).

Outside of the controlled drug delivery area, there has been little utilization or development of microcapsule or polymeric devices for controlled release of materials embedded within the polymers. Even within the area of controlled drug delivery, it has been difficult, if not impossible, to achieve the desired release kinetics for a bioactive substance from either polymer films or microcapsules. The preferred type of release occurs relatively linearly over time ("zero order kinetics"), not irregularly as a function of variations within the polymer chains or the relative thicknesses of different portions of the device. Even with spheres of apparently uniform diameter, linear release is not obtained.

It is therefore an object of the present invention to provide a method and means for forming a polymer matrix containing a uniform distribution of microcapsules or microspheres including bioactive or other compounds.

It is another object of the present invention to provide a method and means for releasing bioactive or other compounds from a polymeric matrix at a desired rate and quantity.

It is a further object of the present invention to provide a method and means for controlled release of bioactive or other compounds from a polymer matrix which can be controlled by external stimuli such as light, temperature, or ultrasound.

It is yet another object of the present invention to provide a method and means for forming a permeable or porous polymeric membrane after the polymer is polymerized and formed into the desired shape.

SUMMARY OF THE INVENTION

The present invention is a method and means for constructing polymer composites containing microcapsules or microspheres. The polymeric matrices and the microspheres or microcapsules may be formed of either biodegradable or non-degradable polymers including polyanhydrides, polyorthoesters, polystyrene, polyurethane, polypropylene, polymethacrylate, polyglycolic acid, polylactic acid, and other known polymers. As used herein, microcapsules are spheres having a central cavity and microspheres are solid spheres (as used herein, "spheres" refers generally to either microcapsules or microspheres).

In one embodiment, the spheres contain compound to be released. In another embodiment, the spheres are removed from the matrix after polymerization of the surrounding matrix to form a permeable or porous polymeric membrane. The diameter of the spheres in the polymer matrix may be optimized to control the rate of release and the quantity of release or the resulting pore size.

A variety of polymer combinations can be designed to encapsulate bioactive materials including drugs, insecticides, and herbicides and inorganic or organic compounds such as dyes. flame retardants, or solvents.

In one variation of the first embodiment, spheres containing an encapsulated compound are homogeneously dispersed within a polymer matrix for release of the compound following exposure of the matrix to heat, UV light, or ultrasound. In another variation of this embodiment, erodible polymers or a combination of erodible and non-degradable polymers are used to construct spheres such that release occurs as a function of the degradation of the erodible polymer. In variations of the second embodiment, release of an encapsulated compound, such as a foaming agent, or degradation of spheres formed of degradable polymers is used to modify the polymeric matrix, for example, to create a porous structure.

The polymer composites have a variety of uses. For example, when carbon tetrachloride is encapsulated within spheres embedded within a polymeric matrix having a relatively low melting point, the system forms an effective flame retardant barrier. Porous polymer matrices formed through release of a gas-forming material within the microcapsules embedded within the matrix have applicability as transdermal drug delivery devices, vascular grafts, and wound coverings. The latter is particularly useful since the pores can be created after polymerizing and situating the composite. Due to the extremely desirable release kinetics of encapsulated compounds from immobilized microcapsules, the composites are especially useful for controlled drug delivery.

DETAILED DESCRIPTION OF THE INVENTION

The present invention is a method and means for constructing polymer composites containing microcapsules or microspheres for subsequent release of encapsulated compounds or modification of the polymer matrix.

In one embodiment a compound is encapsulated within microcapsules or incorporated into microspheres which are then uniformly embedded in a polymer matrix. Upon exposure to a specific stimuli or degradation of the microcapsule or microsphere, the compound is released. In a second embodiment the compound is released to modify the surrounding polymeric matrix.

Microcapsules and microspheres (jointly referred to herein as "spheres") can be constructed using methods known to those skilled in the art. For example, spheres can be formed by interfacial polymerization, hot melt microencapsulation, solvent removal, solvent evaporation, or methods such as those described in U.S. Ser. No. 045,840 filed May 1, 1987 by Edith Mathiowitz and Robert S. Langer entitled "Multiwall Polymeric Microcapsules" and U.S. Ser. No. 025,409 filed Mar. 13, 1987 by Edith Mathiowitz et al. entitled "Preparation of Polyanhydride Microspheres and Use in Controlled Drug Delivery". Exemplary methods applied to specific polymers are summarized as follows.

Polyamide microcapsules can be constructed by interfacial polymerization using the method of Edith Mathiowitz et al. in "Photochemical Rupture of Microcapsules: A Model System", *J. App. Polym. Sci.*, 26 809 (1981). Briefly, an aqueous solution of the amine and polyvinyl alcohol are added to a suspension of a benzene:xylene solution (2:1, v/v) of the dichloride in water. Azobisisobutironitrile (AIBN) and/or azobenzene are added to the organic solution. The polycondensation reaction is allowed to continue for a desired period of time. Microcapsules are separated by decantation, repeatedly washed with distilled water and dried by rapid washing with acetone. As described, the amine:chloride ratio, in equivalent units, are held constant.

Polyanhydride microspheres can be formed by hot melt microencapsulation by mixing melted polymer with solid particles of the substance to be encapsulated, such as a dye or drug. This method, applicable only when the substance to be encapsulated is stable at the melting point of the polymer, is described by E. Mathiowitz and R. Langer in "Polyanhydride Microspheres as Drug Carriers I. Hot Melt Encapsulation", *J. Controlled Release*, 5, 13–22 (1987). The mixture is suspended in a non-miscible solvent, heated 5° C. above the melting point of the polymer, and stirred continuously. Once the emulsion is stabilized, it is cooled until the core material solidifies. The solvents used to make the microcapsules in the following examples were silicon and olive oil. The particle size of the compound to be encapsulated was selected to always be less than 50 microns. The spheres are washed by decantation with petroleum ether to produce a free flowing powder.

One method of preparing polyanhydride spheres by solvent removal is described by Edith Mathiowitz et al. in "Polyanhydride Microspheres as Drug Carriers." II. "Microencapsulation by Solvent Removal", *J. Appl. Poly. Sci.* (1987). As applied to the production of polycarboxyphenoxypropane:sebacic acid (20:80) 16,000 molecular weight spheres, 1 g polymer is dissolved in 1 ml methylene chloride. The compound to be encapsulated is mixed into the solution, dropped into silicon oil (Dow Chemical Co, Midland, MI) containing between 1 to 5% of Span ™ 85 and stirred. After 1 hour, petroleum ether is added to the mixture and stirring continued for another hour. The spheres are isolated by filtration, washed with petroleum ether, and dried overnight in a lyophilizer.

When higher molecular weights polymers with higher percentages of carboxyphenoxypropane (CPP) are used, a different method is required. 2 g polymer is dissolved in 10 ml methylene chloride, the compound to be encapsulated is added, and the mixture suspended in silicon oil containing Span ™ 85 and a known amount of methylene chloride. The amount of methylene chloride depends on the type and molecular weight of the polymer used. For example, for pCPP:SA (20:80) having a molecular weight of 30,000 to 40,000, the ratio between the silicon oil and the methylene chloride is 4:1. For pCPP:SA (50:50) having a molecular weight 40,000, the ratio between the silicon oil and the methylene chloride is 1:1. After dropping the polymer solution into the silicon oil, petroleum ether is added and stirred for two hours. Spheres are isolated by filtration, washed with petroleum ether, dried overnight in a lyophilizer, and stored in a freezer.

Methods for preparation of spheres by solvent evaporation, a method well known to those skilled in the art, are described by S. Yolles et al., "Controlled Release of Biologically Active Agents" in *Controlled Release Polymeric Formulation*, D. R. Paul and F. W. Harris, Editors, American Chemical Society Symposium, Washington, D.C. 33, 123–134 (1976); L. R. Beck et al., *Fertil. Steril.*, 31, 545–551 (1979); H. Jaffe, U.S. Pat. No. 4,272,398, June 9, (1981); J. A. Setterstrom et al., *Proceeding of the 1982 Army Science Conference*, Vol 3, 215–226 (West Point, N.Y. 1982); S. Benita et al, *J. Pharm. Sci.*, 73, 1721–1724 (1984); and A. K. Kwong et al., *J. Controlled Release*, 4, 47–62 (1986).

In one embodiment, the spheres are encapsulated within the polymer by dissolving the embedding polymer in an organic solvent to produce a viscous solution and then suspending the spheres in the polymer solution. The polymer is preferably dissolved in just enough organic solvent to produce a viscous solution. This allows for a more homogeneous suspension of spheres. Highly volatile solvents are selected to dissolve the embedding polymer so as to enhance rapid solidification of the solution and thereby prevent the spheres from settling. The organic solvent must not dissolve the polymeric spheres.

Examples of polymer-solvent systems include: polystyrene in $CH_2Cl_2$, ethylenevinyl acetate in $CH_2Cl_2$, polyurethane in tetrahydrofuran, polyvinylamide in water, and polystyrene in toluene.

Another way to embed the spheres in the polymer matrix is to disperse the spheres into melted polymer. Still another method is to mix the spheres with particles of polymer, then compress the mixture into the desired shape. Caution must be exercised however to prevent rupture of microcapsules using this method.

The types of polymer used to form the spheres and the matrix are determined by the application, taking into consideration possible interactions between the polymers used to form the spheres and the polymer used for the matrix. Polymers which are not miscible in each other are preferred so that the integrity of the spheres is maintained during the formation of the composite. In some biomedical applications, it is desirable to use polymer for the spheres which erode before the polymers forming the matrix. For other applications, a non-erodible matrix polymer in combination with spheres formed of erodible polymers is favored. For instance, small erodible spheres of polylactic acid or polyanhydrides in a non-erodible matrix of polyurethane or polystyrene can be employed to form a porous structure.

A unique application is the production of membranes with changing or variable porosity, which is achieved by rupture or erosion of encapsulated spheres. Photochemical rupture of microcapsules is described by E. Mathiowitz et al. in *J. Appl. Poly. Sci.*, 26, 809–822 (1981). Temperature release is obtained by heating the microcapsules described in (Mathiowitz, et al. in *J. Appl. Poly. Sci.*). Release using ultrasound is described by Kost et al in "Ultrasonic Modulated Drug Delivery Systems" in *Polymers in Medicine: Biomedical and Pharmaceutical Applications II.*, E. Chellini, editor (1987).

The type of release is an important factor in determining which polymers to use, as well as the method utilized to make the composite and whether microcapsules or microspheres are preferred. For example, sudden versus sustained release have different requirements. When sudden release is desired, the reservoir-type device encapsulated inside a film is selected (polyamide microcapsules inside a polyurethane matrix). For controlled release of bioactive substances in vivo, one would choose biodegradable or rupturable microcapsules or microspheres in a biodegradable implant shaped appropriately for the site and rate of release (polyanhydride microspheres or microcapsules inside a polyanhydride matrix). For creation of a vascular graft, rapidly erodible or rupturable microspheres can be entrapped within an extruded tube-shaped slower degrading polymer matrix. Rapid erosion of the spheres results in pores for immediate cell seeding and vascularization, with the matrix providing support until cell growth becomes confluent and acquires structural integrity.

A major advantage of the present invention is the versatility of application. Structures ranging from flame retardant films to erodible vascular grafts and drug delivery systems to porous polymeric membranes can be constructed. The size and shape of the matrix, and means used to configure it, can be tailored as needed. Similarly, the type of polymer, the diameter and fabrication of the spheres, and the content of the spheres can be fashioned as dictated by the function.

As used herein, "compounds" includes both liquid and solid drugs, insecticides, herbicides, other bioactive compounds, inorganic and organic solvents, dyes, foaming agents, flame retardants, antioxidants, biocidal compounds, lubricants, surfactants, etc. Substances to be released can be dissolved in the embedding polymer, dissolved into the polymer forming the microcapsule or microsphere, or encapsulated within the microcapsules. Considerations in selecting both the polymer-solvent system and the compound to be released include the stability of the compound to be encapsulated, the desired loading of the compound to be released (g compound/g polymer or ml compound/g polymer), the release kinetics, the solubility of the compound in the polymers, and the means by which the compound is to be released.

For example, flame retardant polymer film can be produced by encapsulating carbon tetrachloride within polyamide microcapsules which are then embedded in a polyurethane or polystyrene polymer matrix. The matrix and microcapsule polymers rupture upon exposure to a preselected temperature, thereby releasing the carbon tetrachloride. Other flame retardant materials could be used, as could foaming agents, surfactants, or lubricants whose release in the presence of high heat is desired. The microcapsule-polymer matrices could also be used as a delivery system for an antioxidant or a preservative within a sealed container where release of the encapsulated compound is achieved by exposure to ultrasound or light. Alternatively, the polymer composites can be used to release fertilizer, insecticides, or herbicides using ultrasound, light or temperature as the release mechanism.

The present invention is further described by the following non-limiting examples.

EXAMPLE 1

Release of a Dye From Microcapsules not Embedded in a Matrix

Figure 1:
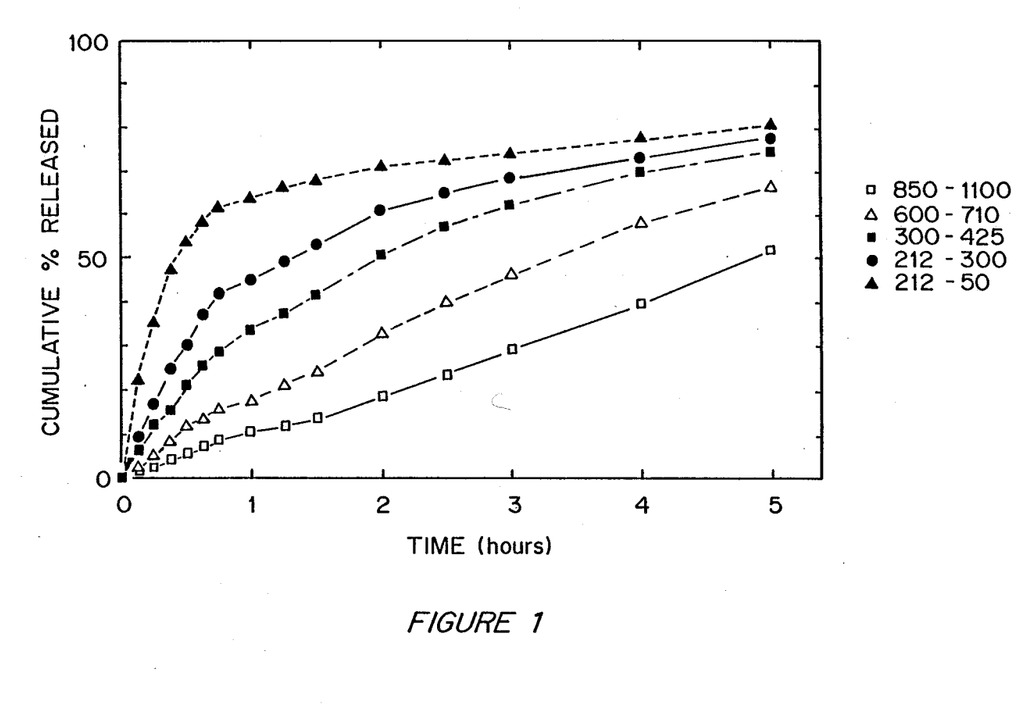
FIG. 1 is a graph of the percent cumulative release of acid orange from microspheres of polycarboxyphenoxy propane copolymerized with sebacic acid p(CCP:SA) (20:80), having diameters of 50 to 212, 212 to 300, 300 to 425, 600 to 710, and 850 to 1100 microns, with 5% loading of acid orange, over time (hours).

For purposes of comparison, polycarboxyphenoxypropane:sebacic acid p(CPP:SA) (20:80) microspheres having diameters between 50 to 212, 212 to 300, 300 to 425, 600 to 710, and 850 to 1100 microns were prepared with 5% acid orange loading. As shown in FIG. 1, when immersed in 40 ml of $NaH_2PO_4$ buffer solution at pH 7.4, between 50 to 80% of the acid orange is released within 5 hours. Release is non-linear in most cases. Release is complete within several hours.

EXAMPLE 2

Figure 2:
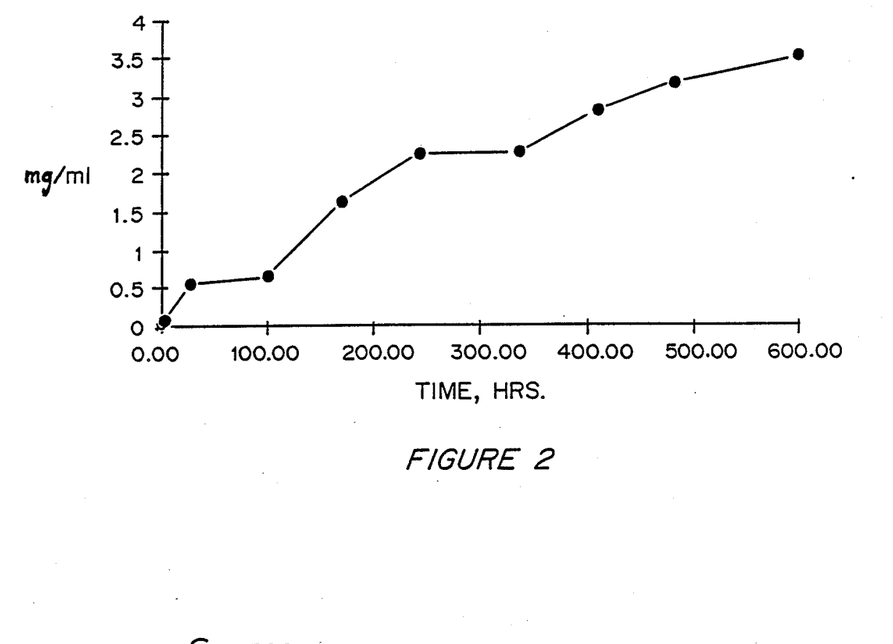
FIG. 2 is a graph of the release of acid orange from microspheres of pCCP:SA (20:80), diameter 300 to 425 microns, embedded in a polyurethane matrix over time (hours).

Release of Acid Orange From p(CPP:SA) (20:80) Microspheres Embedded in Polyurethane Approximately zero order release kinetics are demonstrated by FIG. 2 which shows release of acid orange from p(CPP:SA) (20:80) microspheres with 5% loading of acid orange which are embedded in a matrix of polyurethane. The microspheres have a diameter of 300–425 microns. The polymer matrix has a diameter of 1 mm. Release occurs over an extended period of time, approximately one month. This is in sharp contrast to the release displayed in FIG. 1. Not only is the compound released over a greater period of time, but a substantially more linear release is obtained at the initial stages.

EXAMPLE 3

Figure 3:
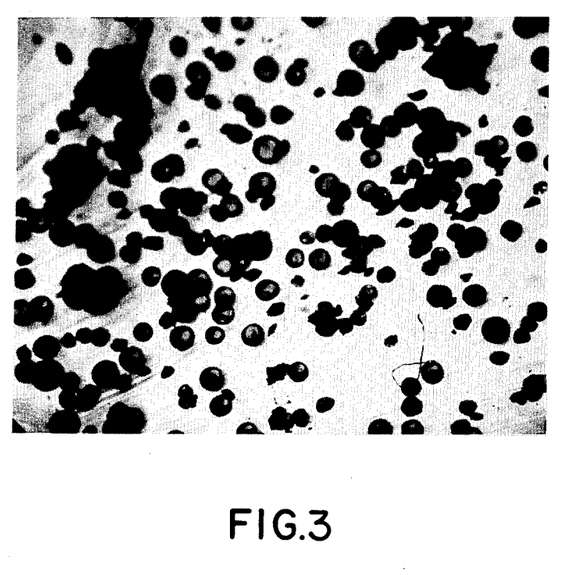
FIG. 3 is a photograph of polyamide microcapsules embedded in polystyrene ($\times 60$).
Figure 4A:
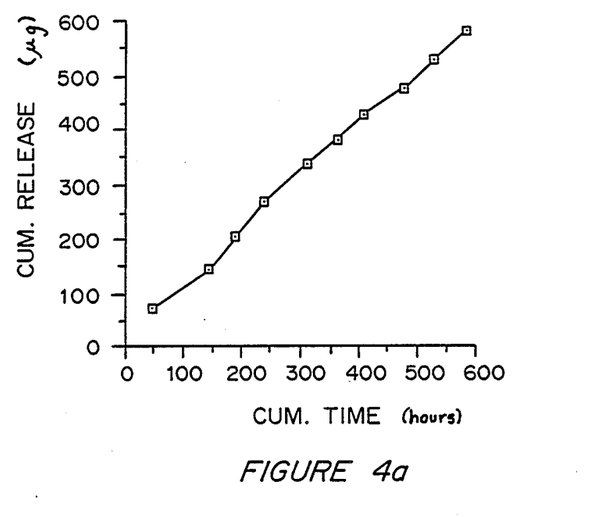
FIG. 4 are graphs of the cumulative release of heparin (micrograms) from polylactic acid microspheres with 20% heparin loading embedded in polyurethane (0.2 g microspheres in 1 g polymer) over time (hours). Four identical samples were compared (FIGS. a, b, c, and d).
Figure 4B:
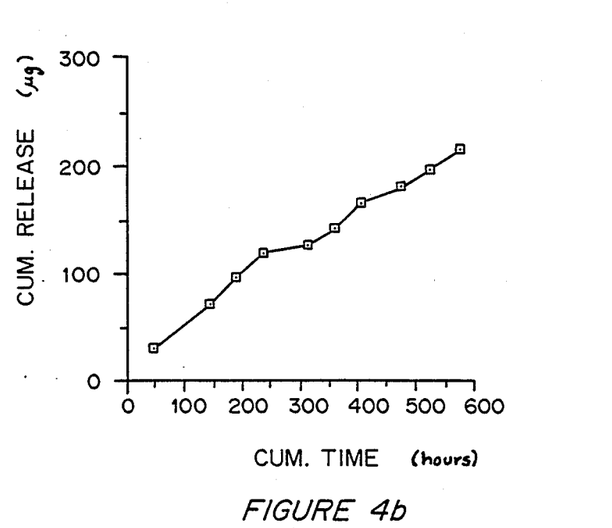
Figure 4C:
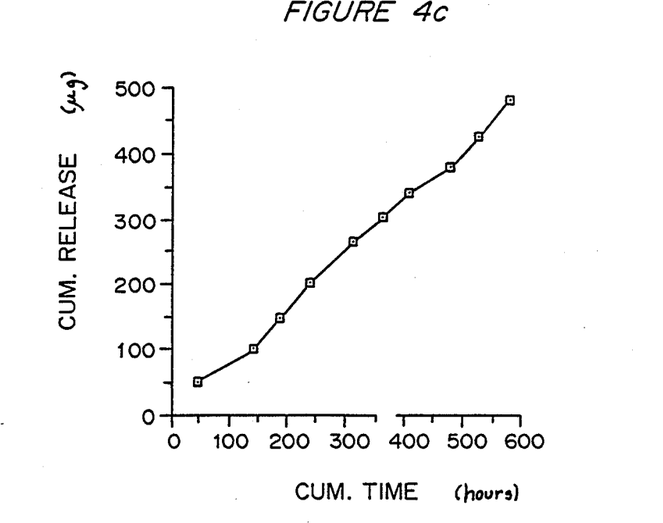
Figure 4D:
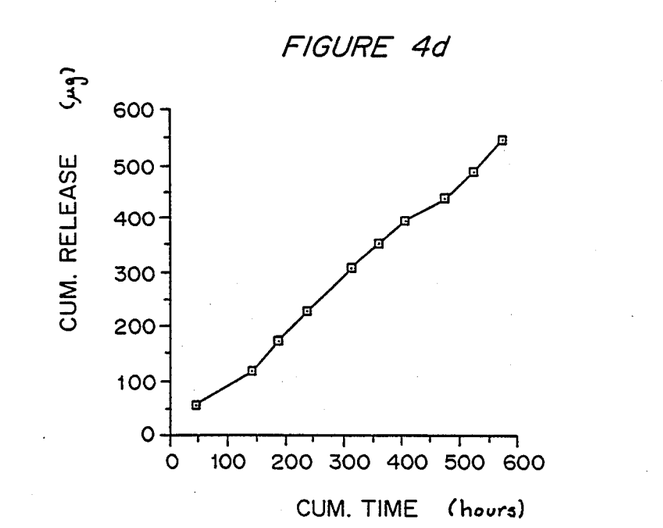

Release From Polyamide Microcapsules Embedded in Polystyrene by Exposure to High Temperature A micrograph showing uniform distribution of polyamide microcapsules throughout the polystyrene matrix is shown in FIG. 3. The matrix was left for 3 days at 100° C., causing the rupture of some of the microcapsules and release of their contents.

EXAMPLE 4

Release of Heparin From Polylactic Acid Microspheres Embedded in a Polyurethane or Polystyrene Matrix Heparin was loaded into polylactic acid microcapsules at 20% loading, i.e., 0.2 g heparin into 0.8 g polymer, which were then embedded in a polyurethane matrix. The release of the heparin from the microcapsules embedded in polyurethane is shown in FIG. 4. Four identical samples are compared in FIGS. 4a, 4b, 4c and 4d. It can be seen that the heparin is released when the matrix is immersed in 40 ml of $NaH_2PO_4$, pH 7.4, with approximately zero order kinetics due to embedding the microspheres in the polyurethane. Further, release is extended over a period of some 600 hours. The results are highly reproducible.

Figure 5:
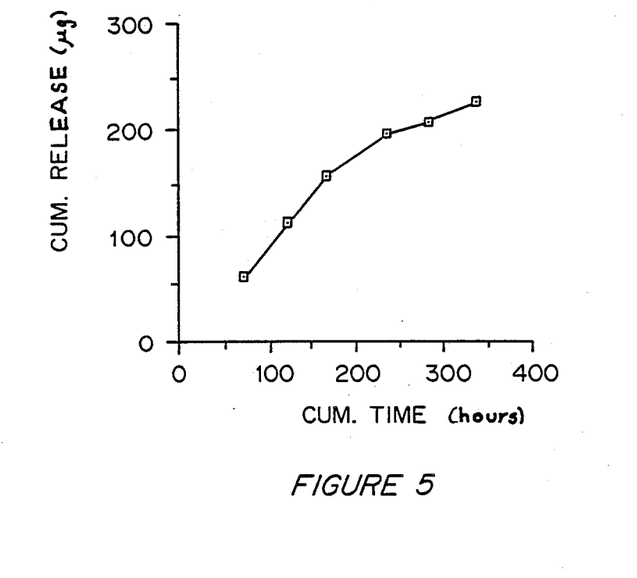
FIG. 5 is a graph of the cumulative release of heparin from polylactic acid microspheres with 20% heparin loading embedded in polystyrene (0.2 g 100–300μ microspheres in 1 g polymer) over time (hours).

Heparin containing microspheres embedded in polystyrene also show approximately zero order release over a period of some 600 hours when immersed in 40 ml of $NaH_2PO_4$, pH 7.4, as shown in FIG. 5. The quantity of release from polystyrene embedded microcapsules is much lower than the release from polyurethane embedded microcapsules. This provides an example of how one can modify release from microcapsules containing the same quantity of compound in order to achieve a different release rate and quantity.

Modifications and variations of the present invention, a method and means employing microcapsules or microspheres embedded in a polymer matrix will be obvious to those skilled in the art from the foregoing detailed description. Such variations and modifications are intended to come within the scope of the appended claims.

We claim:

1. A method for making a composite polymeric device comprising:
   providing a compound to be released,
   incorporating the compound to be released into polymer spheres,
   mixing the polymer spheres into a liquified polymer matrix, and
   solidifying the polymer matrix.

2. The method of claim 1, wherein the polymer spheres are embedded within the liquified polymer matrix by
   dissolving the polymer matrix in an organic solvent in which the polymer spheres are not soluble,
   suspending the polymer spheres in the liquified polymer matrix solution, and
   removing the solvent.

3. The method of claim 2 wherein the liquified polymer matrix is dissolved in an amount of organic solvent which produces a viscous solution.

4. The method of claim 2 wherein the solvent is highly volatile and is rapidly removed by evaporation before the microspheres settle.

5. The method of claim 1, wherein the compound to be released is selected from the group consisting of solvents, lubricants, flame retardants, preservatives, antioxidants, bioactive compounds, insecticides, herbicides, fertilizers, and foaming agents.

6. The method of claim 1, wherein the polymers are selected from the group consisting of polystyrene, polyethylene acetate, polyethylenevinyl acetate, polyurethane, polyamide, polyacrylamide, polymethacrylate, polylactic acid, polyglycolic acid, polyanhydrides, polyorthoester, and derivatives thereof.

7. The method of claim 1, wherein the compound to be released is a drug, at least one polymers is biodegradable, and the drug is released by erosion of the erodible polymer.

8. A method for forming a porous membrane comprising
   providing polymer spheres,
   mixing the polymer spheres within a liquified polymeric matrix, and
   rupturing the polymer spheres to leave pores in the solidified polymeric matrix.

9. The method of claim 8 further comprising encapsulating a gas forming compound within the polymer spheres and releasing the gas when the polymer spheres are ruptured into the continuous polymeric matrix to produce a porous polymeric structure.

10. The method of claim 9 further comprising using the porous structure at a site for cell growth.

11. The method of claim 10 further comprising using the porous structure as a membrane of varying porosity.

12. The polymeric device of claim 3 wherein said polymer matrix can be applied directly to the skin of a patient.

13. The polymeric device of claim 9 wherein said polymer spheres are ruptured within said polymeric matrix by exposure to ultrasound, light, radiation, or temperature,
   said polymer spheres contain a bioactive compound, and
   the bioactive compound diffuses out of said polymeric matrix following rupture of said polymer spheres.

14. The method of claim 1, wherein the liquified polymer matrix is melted.

15. The method of claim 1, wherein the polymer matrix is liquified by heating and solidified by cooling.

16. The method of claim 1, wherein the polymer matrix is solidified by polymerizing monomers of the polymer.

* * * * *